United States Patent
Crook et al.

(10) Patent No.: US 6,224,957 B1
(45) Date of Patent: *May 1, 2001

(54) ANTI-CORROSIVE MATERIAL

(75) Inventors: John A. Crook; John H. Wilson, Jr., both of Birmingham, AL (US)

(73) Assignee: Fulton Enterprises, Inc., Birmingham, AL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/669,111

(22) Filed: Jun. 24, 1996

(51) Int. Cl.$^7$ ........................................ F16L 9/147
(52) U.S. Cl. ........................ 428/36.91; 428/377; 428/461; 428/516; 138/DIG. 6; 138/145; 424/412
(58) Field of Search ................... 428/516, 36.91, 428/461, 34.6, 34.7, 36.9, 377; 523/122; 424/411, 412; 138/DIG. 6, 143

(56) References Cited

U.S. PATENT DOCUMENTS

| | | | |
|---|---|---|---|
| 2,937,665 | 5/1960 | Kennedy | 138/145 |
| 3,024,153 | 3/1962 | Kennedy | 156/187 |
| 3,033,724 | 5/1962 | Stokes | 156/187 |
| 3,157,204 | 11/1964 | Phillips | 138/137 |
| 3,223,571 | 12/1965 | Straughan | 156/392 |
| 3,425,954 | 2/1969 | Ruzevick et al. | 252/392 |
| 3,469,002 | 9/1969 | Moyer | 424/413 |
| 3,565,747 | 2/1971 | Vincent et al. | 428/327 |
| 3,687,765 | 8/1972 | MacLean et al. | 156/185 |
| 3,692,619 | 9/1972 | Wedekind et al. | 428/190 |
| 3,877,490 | 4/1975 | Tsubouchi et al. | 138/141 |
| 4,035,546 * | 7/1977 | Ruppert, Jr. | 428/332 |
| 4,051,066 | 9/1977 | Miksic et al. | 252/389.5 |
| 4,211,595 | 7/1980 | Samour | 156/187 |
| 4,213,486 | 7/1980 | Samour et al. | 138/143 |
| 4,254,165 | 3/1981 | Phelps et al. | 427/183 |
| 4,290,912 | 9/1981 | Boerwinkle et al. | 252/389.3 |
| 4,321,297 | 3/1982 | Adelman | 428/292.7 |
| 4,331,480 * | 5/1982 | Gutman et al. | 106/18.33 |
| 4,374,174 | 2/1983 | Stricklin et al. | 428/341 |
| 4,472,231 | 9/1984 | Jenkins | 156/307.5 |
| 4,499,136 | 2/1985 | Nakamura et al. | 428/206 |
| 4,533,435 | 8/1985 | Intili | 162/161 |
| 4,557,966 | 12/1985 | Weil | 428/209 |
| 4,617,328 * | 10/1986 | Lui | 523/122 |
| 4,631,302 * | 12/1986 | Supcoe et al. | 523/122 |
| 4,670,499 * | 6/1987 | Bonnke et al. | 524/427 |
| 4,752,629 * | 6/1988 | Proudlock et al. | 523/122 |
| 4,789,692 * | 12/1988 | Rei et al. | 523/122 |
| 4,824,705 | 4/1989 | Persson et al. | 428/35.9 |
| 4,853,297 | 8/1989 | Takahashi et al. | 428/623 |
| 4,973,448 | 11/1990 | Carlson et al. | 422/9 |
| 4,983,449 | 1/1991 | Nee | 442/171 |
| 4,988,236 * | 1/1991 | Ramsey et al. | 405/157 |
| 5,006,185 | 4/1991 | Anthony et al. | 156/193 |
| 5,139,700 | 8/1992 | Miksic et al. | 252/389.54 |
| 5,209,869 | 5/1993 | Miksic et al. | 252/389.54 |
| 5,320,778 * | 6/1994 | Miksic et al. | 252/389.54 |
| 5,465,527 * | 11/1995 | Able | 47/33 |
| 5,525,426 * | 6/1996 | Kulzick et al. | 428/412 |

* cited by examiner

*Primary Examiner*—Paul Thibodeau
*Assistant Examiner*—D. Lawrence Tarazano
(74) *Attorney, Agent, or Firm*—Robert J. Veal; Robert M. Jackson; Burr& Forman LLP

(57) ABSTRACT

An improved anti-corrosive material used to protect buried conduits from corrosion. The material is a multi-layered co-extruded, calendered, or laminated polyolefin. The material has an outer layer, or environment contacting layer, preferably comprised of a low density polyethylene having characteristically strong tensile strength and elongation properties to provide conventional protection from soil, water, air, or other potentially damaging elements. The material has a center layer preferably comprised of a high density polyethylene having superior tensile strength to provide a high density barrier between the outer layer and an inner layer. The inner layer, or conduit contacting layer, is preferably comprised of a low density polyethylene impregnated with a biocide, a volatile corrosion inhibitor (VCI), or both. The biocide and VCI are able to migrate through the low density polymer matrix but the rate of migration of the biocide is considerably slowed through the high density polymer and the VCI is essentially unable to penetrate it. Thus, the biocide and VCI are substantially prevented from escaping into the surrounding environment, but rather, are trapped within a "protection zone" immediately adjacent the conduit surface to provide extended protection against corrosion.

16 Claims, No Drawings

ANTI-CORROSIVE MATERIAL

FIELD OF THE INVENTION

The present invention relates to an improved anti-corrosive material. More particularly, the present invention relates to a multi-layered material used to encase buried conduits to prevent corrosion.

BACKGROUND OF THE INVENTION underground conduits are ubiquitous in modern society. Conduits are used for carrying a wide variety of substances, including water, natural gas, oil, and sewage. In the past, these conduits have been typically comprised of plastics, concrete, or metals. One of the major problems with buried conduits comprised of concrete, concrete with metal reinforcements, or metal, is corrosion. The severity and rate of corrosion is dependent on the type of material comprising the conduit and the environment in which the conduit is buried. For example, ductile iron pipe (DIP) typically exhibits a low risk to severe corrosion compared to other metals. However, a rapid increase in the corrosion rate can be initiated by oxygenated water, tidal action, or specific soil types as soils containing sulfides. Because of high costs associated with removal and replacement of corroded conduits, the industry has expended substantial resources to solve this problem.

Initially, conduits were covered with paint coatings, wraps, or other materials to separate the conduit surfaces from the environment. Later, barrier films of polyethylene were used to protect DIP conduits. By insulating the exposed surfaces from soil, electrical currents, and oxygenated water, corrosion is usually prevented. However, due to improper installation, tears and punctures to the barrier film occurring during the installation and backfill process, free flow of water from tidal action, or soil or water becoming entrapped between the film and the conduit surface, actual corrosion still occurs in many cases. The industry has attempted to solve these problems by using more durable barrier films to encase the conduit surfaces, such as high density cross-laminated polyethylenes (HDCLPE). The superior impact strength, tear resistance, and tensile strength of HDCLPE has reduced some of the problems associated with the installation and backfill process; however, HDCLPE does not adequately address or control the problem of corrosion. Since there has not been an adequate alternative, present industry standards typically use either an 8 mil low density polyethylene (LDPE) film or a 4 mil HDCLPE film, a mil being equal to one thousandth of an inch (0.0254 millimeter), to wrap around the conduits for protection against corrosion.

Polyethylenes, as well as other plastic films, limit the free flow of water against the conduit surfaces, thereby reducing available oxygen. Any moisture which becomes trapped between the film and the conduit surface will eventually become deaerated. A problem arises where deaerated water levels are attained in the presence of sulfate reducing bacteria. Many anaerobic bacteria, such as *Desulfovibrio desulfunicans*, thrive in certain fresh water, brackish water, sea water, sulfate soils, or warm soil conditions. These bacteria act as a catalyst to initiate or augment the rate of corrosion in an environment that is normally adverse to corrosion. Additionally, other types of bacteria are believed to play a part in corrosion propagation and it appears that bacteria are also responsible for degradation of the polyethylene film. A possible solution to this problem is to treat the materials used to encase the conduit with bactericides. However, most bactericides are topical and water soluble, thereby offering only initial protection. Since conduits are buried for decades, this would not provide adequate long-term protection.

Another possible solution is to use certain volatile corrosion inhibitors (VCIs) which can be added to eliminate or reduce the presence of corrosion. An example of a commonly used VCI is illustrated in U.S. Pat. No. 3,425,954. These VCIs can be used to prevent conditions from developing inside the film barrier which are favorable to corrosion. VCIs work at a micron level to passivate the surface of metal with a passive film, thus reducing the chemical reactivity of its surface. VCIs are normally used in kraft papers for short term protection of metal parts, as illustrated in U.S. Pat. No. 4,557,966; however, paper is not suitable to be buried. VCIs could be added to the polyethylene film, but the effectiveness will be shortened since the vapor tends to escape from the film, thus preventing extended protection.

From the foregoing it may be seen that a need exists for an improved anti-corrosive material for protecting conduits buried in conditions favorable to corrosion.

SUMMARY OF THE PRESENT INVENTION

It is the object of the present invention to provide an improved anti-corrosive material which is superior to those presently used to protect buried conduits.

It is another object of the present invention to provide a material which contains a biocide to prevent bacterial-induced or enhanced corrosion.

It is still another object of the present invention to provide a material which contains a biocide to prevent bacterial-induced or enhanced degradation of the material.

It is a further object of the present invention to provide a material which contains volatile corrosion inhibitors to prevent corrosion.

It is still a further object of the present invention to provide a material which is co-extruded, calendered, or laminated into a multi-layered material comprising a conduit contacting layer having any anti-corrosive agents, such as biocides or volatile corrosion inhibitors, impregnated therein such that the anti-corrosive agents can migrate within the conduit contacting layer to contact the conduit surface and prevent corrosion.

It is yet a further object of the present invention to provide a material which is co-extruded, calendered, or laminated into a multi-layered material further comprising a barrier layer adjacent the conduit contacting layer which prevents the anti-corrosive agents from penetrating the barrier layer and escaping into the surrounding environment.

These and other objects of the present invention are accomplished through the use of an improved anti-corrosive material used to protect buried conduits from corrosion. The material is a multi-layered co-extruded, calendered, or laminated polyolefin. The material has an outer layer, or environment contacting layer, preferably comprised of a low density polyethylene having characteristically strong tensile strength and elongation properties to provide conventional protection from soil, water, air, or other potentially damaging elements. The material has a center layer preferably comprised of a high density polyethylene having superior tensile strength to provide a high density barrier between the outer layer and an inner layer. The inner layer, or conduit contacting layer, is preferably comprised of a low density polyethylene impregnated with a biocide, a volatile corrosion inhibitor (VCI), or both. The biocide and VCI are able to migrate through the low density polymer matrix but the rate of migration of the biocide is considerably slowed through the high density polymer and the VCI is essentially unable to penetrate it. Thus, the biocide and VCI are substantially prevented from escaping into the surrounding environment, but rather, are trapped within a "protection zone" immediately adjacent the conduit surface to provide extended protection against corrosion.

These and other objects and advantages of the invention will become apparent from the following detailed description of the preferred embodiment of the invention.

DETAILED DESCRIPTION OF THE PREFERRED EMBODIMENT

An anti-corrosive material embodying features of the invention is comprised of a multi-layered co-extruded, calendered, or laminated polyolefin. The preferred embodiment of the present invention is comprised of 3 layers with a total thickness of 8 mils, to conform to the industry standard film thickness. It is to be understood that the following description is for purposes of illustration only and that the thickness of the film as a whole or the individual layers, or the method of producing the layers, can be altered from that described herein without departing from the spirit of the invention. Additionally, the polyolefin of choice is polyethylene but others such as polypropylene, ethylene/vinyl acetate copolymers, vinyl acetate/vinyl chloride copolymers, or polyvinyl chloride could be substituted.

The outermost layer, or environment contacting layer, provides conventional protection from soil, water, air, or other potentially damaging elements. The outermost layer typically comprises 4 mils of low density polyethylene (LDPE), preferably linear low density polyethylene (LLDPE), having characteristically strong tensile strength and elongation properties. This deters punctures and tears during handling and the backfill process. LDPE has a density range between approximately 0.910 to 0.925. The purpose of the outer layer is to provide conventional protection; therefore, biaxially oriented LDPE, medium density polyethylene (MDPE), or high density polyethylene (HDPE) could be substituted. MDPE has a density range between approximately 0.926 to 0.940. The center layer typically comprises 2 mils of HDPE, having a density greater than approximately 0.94. This layer possesses superior tensile strength and provides a high density barrier acting to prevent any anti-corrosive agents impregnated within the innermost layer from migrating through the center layer and escaping into the environment.

The innermost layer, or pipe contacting layer, preferably comprises a 2 mil LDPE, although a linear or biaxially oriented LDPE or MDPE could be substituted. This layer is impregnated with a biocide, a volatile corrosion inhibitor (VCI), or both. Both the biocide and VCI must be able to withstand the temperature required to melt and process the polyolefin. The biocide is preferably a contact inhibitor for preventing the growth of certain corrosion causing bacteria. The biocide can be selected for killing a broad spectrum of organisms, such as bacteria, molds, fungi, etc., or it can be specific, such as a bactericide for eliminating sulfate reducing bacteria or other corrosion-inducing bacteria. Some biocides which are presently used in kraft paper and the like which are suitable for impregnation into the LDPE are, halogenated aromatic nitriles, imazilil sulfate salts, 3,5,3', 4'tetrachlorosalicylanilide, dichlorophene, hexachlorophene, dioxin, ethyl benzoate, methyl benzoate, and methyl p-hydroxy-benzoate. See e.g. U.S. Pat. Nos. 3,469,002, 4,401,712, and 4,533,435.

The biocide is blended into molten LDPE resin which will be used in forming the innermost layer. The LDPE and biocide are typically mixed at about 400 degrees Fahrenheit; however, the temperature should not exceed about 425 degrees Fahrenheit because the biocide can begin to irreversibly denature or evaporate. The molten material is then ready to be extruded to form the innermost layer. The final concentration of biocide is approximately 0.05% to 2.0% by weight, although this can vary depending on the type of biocide used and the environment to be used in. The biocide is partially bound to the polyolefin matrix such that some biocide is retained within the polymer matrix to prevent bacterial growth, while unbound biocide will slowly migrate through the polymer matrix toward the conduit surface to prevent bacterial growth. The migration of the biocide is considerably slowed by the high density center layer; thus the biocide is kept within a "protection zone" comprising the inner layer and conduit surface. The slow migration of the biocide within the polymer matrix towards the conduit provides low levels of biocide to the conduit surface for an extended period of time.

The VCI is preferably comprised of nitrates or nitrites, which are proven effective corrosion inhibitors, although other VCIs could be used, such as triazoles, carbonates, phosphates, molybdates, and aliphatic or aromatic amines. See e.g. U.S. Pat. Nos. 4,973,448 and 5,139,700. VCIs operate by passivating the metal, or reducing the chemical reactivity of its surface; thus stopping or reducing corrosion rates that occur under the film. Typically, VCI is blended with molten polyethylene resin, at about 400 degrees Fahrenheit, which will be used in forming the innermost layer; however, again the temperature should not exceed about 425 degrees Fahrenheit because the VCI will evaporate. The molten material is then ready to be extruded to form the innermost layer. The final concentration of VCI is typically between approximately 1% to 5% by weight of the innermost layer, preferably 2% to 3%, although this can vary depending on the type of VCI used and the environment to be used in.

The VCI is not bound to the polyolefin matrix and LDPE has a measurable rate of moisture and vapor transmission, thus the VCI slowly migrates toward the conduit since it is too large to pass through the center layer, resulting in long-term protection of the conduit surface. Some gas transmission rates of LDPE and HDPE are:

|  | Oxygen[1] | Water Vapor* |
| --- | --- | --- |
| LDPE | 500–450 | 1–2 |
| LDPE (Biaxially Oriented) | 350–400 | 0.3–0.5 |
| LDPE (Linear) | 300–400 | 0.5–1.0 |
| HDPE | 150–200 | 0.3–0.5 |

[1]cc mil/100 sq. in./24 hrs. at 72 degrees Fahrenheit
*gm mil/100 sq. in./24 hrs. at 100 degrees Fahrenheit, 90% Relative Humidity After the materials for each layer have been prepared, the material is co-extruded, calendered, or laminated into a 3 layered product. The process of co-extruding, calendering, and laminating multi-layered films is well known in the art and will not be described herein. It is especially important to note that the innermost layer of the anti-corrosive material may be impregnated with the biocide, the VCI, or both, depending on the intended use. Additionally, the anti-corrosive material could be comprised from only one layer of polyolefin having the anti-corrosive agents impregnated therein to a material having a plurality of layers with any number of layers having the anti-corrosive agents impregnated therein. The spirit of the present invention is the incorporation of biocide or VCI into polyolefin films used for protecting buried materials susceptible to corrosion, which can include underground conduits, storage tanks, building foundations, etc. The VCI has an additional benefit of controlling certain bacterial growth and the biocide has an additional benefit of limiting bacterial growth responsible for other problems, such as degradation of rubber gaskets or the polyethylene film. Another benefit of using the multi-layered material is seen where some municipalities require color coating for underground conduits indicating the class of materials contained within the conduit. With the multi-layered product, only the exterior layer must be colored, thus reducing the costs from color additives.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. An apparatus for carrying fluids, comprising:
   a conduit comprising metal; and
   a multi-layered polyolefin film comprising a single anti-corrosive layer in abutment with a surface of said conduit, said anti-corrosive layer having a bactericide for killing corrosion-inducing bacteria on the surface of said conduit, and a barrier layer adjacent said anti-corrosive layer, said barrier layer having a permeability resistant to migration of said bactericide therethrough such that said bactericide is maintained in an anti-corrosion zone comprising said anti-corrosive layer and the surface of said conduit, wherein said bactericide is selected from a group consisting of halogenated aromatic nitriles, imazilil sulfate salts, 3,5,3', 4'tetrachlorosalicylanilide, dichlorophene, hexachlorophene, dioxin, ethyl benzoate, methyl benzoate, and methyl p-hydroxy-benzoate.

2. The apparatus of claim 1, wherein the concentration of said bactericide in said anti-corrosive layer is between 0.05% to 2.0% by weight.

3. The apparatus of claim 1, wherein said barrier layer comprises a high density polyethylene.

4. The apparatus of claim 1, wherein said bactericide is specific for killing sulfate-reducing anaerobic bacteria.

5. The apparatus of claim 1, wherein said conduit comprises ductile iron pipe.

6. The apparatus of claim 1, wherein said polyolefin film is selected from the group consisting of polyethylene, polypropylene, ethylene/vinyl acetate copolymers, vinyl acetate/vinyl chloride copolymers, and polyvinyl chloride.

7. The apparatus of claim 1, wherein said anti-corrosive layer comprises a medium density polyethylene.

8. The apparatus of claim 1, wherein said anti-corrosive layer comprises a low density polyethylene.

9. An apparatus for carrying fluids, comprising:
   a conduit comprising metal; and
   a polyolefin film in abutment with a surface of said conduit, said film comprising a bactericide for killing corrosion-inducing bacteria on the surface of said conduit, wherein said polyolefin film comprises a single anti-corrosive layer having said bactericide and a barrier layer having a permeability resistant to migration of said bactericide therethrough, wherein said anti-corrosive layer is in abutment with the surface of said conduit so that said bactericide is maintained in an anti-corrosion zone, wherein said bactericide is selected from a group consisting of halogenated aromatic nitrites, imazilil sulfate salts, 3,5,3', 4'tetrachlorosalicylanilide, dichlorophene, hexachlorophene, dioxin, ethyl benzoate, methyl benzoate, and methyl p-hydroxy-benzoate.

10. The apparatus of claim 9, wherein the concentration of said bactericide in said anti-corrosive layer is between 0.05% to 2.0% by weight.

11. The apparatus of claim 9, wherein said polyolefin film is selected from the group consisting of polyethylene, polypropylene, ethylene/vinyl acetate copolymers, vinyl acetate/vinyl chloride copolymers, and polyvinyl chloride.

12. The apparatus of claim 9, wherein said anti-corrosive layer comprises a low density polyethylene.

13. The apparatus of claim 9, wherein said anti-corrosive layer comprises a medium density polyethylene.

14. The apparatus of claim 9, wherein said barrier layer comprises a high density polyethylene.

15. The apparatus of claim 9, wherein said bactericide is specific for killing sulfate-reducing anaerobic bacteria.

16. The apparatus of claim 9, wherein said conduit comprises ductile iron pipe.

* * * * *